United States Patent [19]

Khanna et al.

[11] Patent Number: 4,997,959
[45] Date of Patent: Mar. 5, 1991

[54] PROCESS FOR THE PRODUCTION OF ALPHA-6-DEOXYTETRACYCLINES

[75] Inventors: Jagmohan Khanna; Kiran Bala; Inder P. S. Grover, all of New Delhi, India

[73] Assignee: Ranbaxy Laboratories Limited, India

[21] Appl. No.: 337,288

[22] Filed: Apr. 13, 1989

[51] Int. Cl.$^5$ .................. C07C 103/19; C07C 237/00
[52] U.S. Cl. .................................................. 552/206
[58] Field of Search ...................... 260/351.5; 552/206

[56] References Cited

U.S. PATENT DOCUMENTS

| | | | |
|---|---|---|---|
| 2,984,986 | 5/1961 | Hill | 61/28 |
| 3,200,149 | 8/1965 | Blackwood | 552/206 |
| 3,444,198 | 5/1969 | Korst | 552/206 |
| 3,489,786 | 1/1970 | Dewhirst | 260/465.1 |
| 3,549,780 | 12/1970 | Graneau | 174/21 |
| 3,639,439 | 2/1972 | Dewhirst | 260/429 R |
| 3,703,561 | 11/1972 | Kubicek et al. | 260/683 D |
| 3,907,890 | 9/1975 | Scanio | 252/429 R |
| 3,954,862 | 5/1976 | Morris, Jr. | 552/206 |
| 3,962,131 | 6/1976 | Faubl et al. | 252/429 R |
| 4,001,321 | 1/1977 | Faubl | 552/206 |
| 4,207,258 | 6/1980 | Broggi et al. | 557/206 |
| 4,500,458 | 2/1985 | Villax et al. | 552/200 |
| 4,550,096 | 10/1985 | Page et al. | 502/166 |
| 4,597,904 | 7/1986 | Page | 552/206 |
| 4,743,699 | 5/1988 | Page et al. | 556/23 |

FOREIGN PATENT DOCUMENTS

| | | |
|---|---|---|
| 2216268 | 8/1974 | France . |
| 1121642 | 7/1968 | United Kingdom . |
| 1121643 | 7/1968 | United Kingdom . |
| 1138601 | 1/1969 | United Kingdom . |
| 1219763 | 1/1971 | United Kingdom . |
| 2025403 | 1/1980 | United Kingdom . |

OTHER PUBLICATIONS

Vol. Pin et al., Russian Chemical Rev. 38, 273–289 (1969).
Augustine et al., Ann. N.Y. Sci., 148, 482–91 (1969).
Ruesch et al., Tetrahedron vol. 25, 805–11 (1969).
Wilkinson et al., J. Chem. Soc. 1711–32 (1966).
Knowles et al., Chem. Comm., 1445 (1968).
Horner et al., Angew. Chem. Internat. Edit. 7, 942 (1968).
Frey et al., Chem. Comm., 1069–70 (1969).
Manfredi, Milan, Italy, ACS 70.
Grubbs et al., J. Am. Chem. 93, 3062 (1971).
Kagan et al., J. Am. Chem. Soc. 94, 6429 (1972).
Knowles et al., Chem. Comm. 10, (1972).
Harmon et al., Chem. Rev. 73, 21–52 (1973).
Theissen, J. Org. Chem. vol. 36, 752–757 (1971) (abstract).
Toniolo et al., Chim. Ind. Milan, 58(10), 732 (1976).
Fleet et al., Tetrahedron Letters No. 11, 975–8 (1979).

Primary Examiner—Richard L. Raymond
Assistant Examiner—Raymond Covington
Attorney, Agent, or Firm—Bryan, Cave, McPheeters & McRoberts

[57] ABSTRACT

A process for the hydrogenation of a 6-methylenetetracycline in the production of alpha-6-deoxytetracycline, particularly the antibiotic doxycycline, in the presence of a transition metal complex of the formula $MCl_x(PPh_3)_y$ wherein M is Cu, Co or Ni, x is 1 or 2 and y is 1–3, and a trace of rhodium either as the supported metal or as a rhodium salt, as a hydrogenation catalyst. The desired alpha-6-deoxytetracycline product is produced in high yields and stereospecificities. The process requires the use of substantially cheaper transition metal complexes and only traces of rhodium in the hydrogenation catalyst per mole of the 6-methylene tetracycline hydrogenated.

11 Claims, No Drawings

PROCESS FOR THE PRODUCTION OF ALPHA-6-DEOXYTETRACYCLINES

This invention relates to a process for the preparation of alpha-6-deoxytetracyclines, and more particularly to such a process for the production of the antibiotic doxycycline, viz., alpha-6-deoxy-5-oxytetracycline.

BACKGROUND OF THE INVENTION

The preparation of doxycycline and other alpha-6-deoxytetracyclines was first described in Blackwood et al. U.S. Pat. No. 3,200,149 granted Aug. 10, 1965. That patent described their preparation by the catalytic hydrogenation of a corresponding 6-methylene intermediate, e.g., in the case of doxycycline, 11a-chloro-6-deoxy-6-demethyl -6-methylene-5-oxytetracycline, in the presence of a heterogeneous noble metal catalyst, e.g., palladium on carbon. The Blackwood patent disclosed the production, in yields of up to about 50%, of equimolar proportions of the diastereoisomers (epimers) of the 6-deoxytetracyclines. In the case of doxycycline, the patent disclosed the co-production of the corresponding beta epimer, beta-6-deoxy-5-oxytetracycline.

Subsequent efforts have been directed to the development of syntheses for producing the 6-deoxytetracyclines in greater yields and with greater stereoselectivity of formation of the desired alpha epimers, e.g., doxycycline. Thus, Korst U.S. Pat. No. 3,444,198 granted May 13, 1969, disclosed that the stereoselectivity of formation of the alpha epimers may be increased when the noble metal hydrogenation catalyst is poisoned. The Korst patent described the formation of epimeric mixtures of the 6-deoxytetracyclines in total yields of up to about 60%, with the stereoselective production of the alpha epimers in amounts of up to about 90% of the epimeric product mixtures. The use of other noble metal or noble metal salt compositions as heterogeneous hydrogenation catalysts in the production of doxycycline has also been disclosed in the literature. See, for example, Morris U.S. Pat. No. 3,954,862 granted May 4, 1976, and Page U.S. Pat. No. 4,597,904 granted July 1, 1986.

The use of rhodium halide complexes containing tertiary phosphine ligands, e.g., tris(triphenylphosphine)chloro rhodium (I), as homogeneous hydrogenation catalysts was first described by Wilkinson et al. in 1966 (J. Chem. Soc. 1711-32). Subsequently, a number of soluble complexes of platinum metals, particularly rhodium, with halides and tertiary phosphines or the like, have been described as useful in a variety of regiospecific, stereoselective and asymmetric reduction reactions. See Knowles et a)., Chem. Communs. 1445 (1968); Horner et al., Agnew Chem. Int. Ed. 7, 942 (1968); Vol Pin et al., Russian Chemical Reviews, 38, 273-289 (1969); Augustine et al., Ann. N.Y. Sci., 148, 482-91 (1969); Ruesch et al., Tetrahedron, 25, 807-11 (1969); Piers et al., Chem. Communs. 1069-70 (1969); "Aspects of Homogeneous Catalysis", vol. I. pp. 5-75 (1970); Carlo Manfredi, Milan, Italy; "Homogeneous Catalysis, Industrial Applications and Implications", Vol. 70, Advances in Chemistry Series, American Chemical Society; Grubbs et al., J.Am. Chem. Soc., 93, 3062 (1971); Kagan et al, J.Am. Chem. Soc , 94, 6429 (1972); Knowles et al., Chem. Communs. 10 (1972); and Harmon et al., Chem. Rev. 73, 21-52 (1973). Similar disclosures have been made in the patent literature. See, for example, U.S. Pat. Nos. 3,489,786; 3,549,780; and 3,639,439; and British Patent Nos. 1,121,642; 1,121,643; 1,138,601; and 1,219,763.

The use of tris(triphenylphosphine)chloro rhodium(I) and similar rhodium complexes as homogeneous, stereospecific hydrogenation catalysts in the production of doxycycline and other alpha-6-deoxy-5-oxytetracyclines has also been extensively discussed in the patent literature. See, for example, U.S. Pat. Nos. 3,907,890; 3,962,131; 4,001,321; 4,207,258; 4,500,458; 4,550,096; 4,743,699; and French Patent No. 2,216,268.

The present invention is directed to an improved process for the production of doxycycline and other alpha-6-deoxytetracyclines, wherein the desired alpha epimer is produced in both high yield and stereospecificity, employing a hydrogenation catalyst which is substantially cheaper than catalysts heretofore required. Other objects and advantages of the invention will be apparent from the following description of preferred embodiments thereof.

SUMMARY OF THE INVENTION

This invention comprises an improved process for the preparation of alpha-6-deoxytetracyclines by the hydrogenation of the corresponding 6-methylenetetracyclines, in the presence of transition metal complexes of the formula $MCl_x(PPh_3)_y$ wherein M=Cu, Co or Ni, $x=1-2$, and $y=1-3$, and a trace of rhodium, either in the form of the metal on a suitable support (preferably, rhodium on carbon), or as a rhodium salt (preferably, hydrated rhodium trichloride).

Transition metal complexes of the formula $MCl_x(PPh_3)_y$, wherein M=Cu, $x=1-2$, and $y=1-3$ have been reported in the literature to act as co-catalysts with Pd(II) complexes in the preparation of $\alpha, \beta$-unsaturated carbonyl compounds from the corresponding saturated analogs (J. Org. Chem 36, 752-757 [1971]), as disproportionation catalysts for olefins (U.S. Pat. No. 3,703,561), as catalysts in the Gatterman Koch synthesis of aromatic aldehydes (Chim. Ind. Milan, 58(10), 732 [1976]), and as catalysts in the Ullman reactions of aromatic halides (GB 2,025,403). However, the use of such materials as hydrogenation catalysts in the syntheses of alpha-6-deoxytetracyclines has not previously been reported.

It has now been found that when an appropriate 6-methylenetetracycline substrate is hydrogenated in the presence of such a catalyst system, the corresponding alpha-6-deoxytetracycline is produced in greater than about 95% yield and without the co-production of substantial amounts of the corresponding beta-6-deoxytetracycline epimer. Further, the hydrogenation is effected utilizing a relatively economical transition metal complex and solely a trace of rhodium, as distinguished from the expensive noble metal and noble metal complex catalysts required in previously described processes for the production of doxycycline or other alpha-6-deoxytetracyclines. Increased economies are thus achieved, because of (a) the cheaper transition metal complex, (b) the requirement of only negligible quantities of rhodium, (c) the elimination of expensive purification operations heretofore required for the separation of the undesired beta epimers, and (d) the elimination of the expensive and time consuming recovery/recycling procedures heretofore required to effect re-use of the noble metal catalyst materials.

PREFERRED EMBODIMENT OF THE INVENTION

The process of this invention may be utilized in the production of any of the known alpha-6-deoxytetracyclines, preferably those of the formula

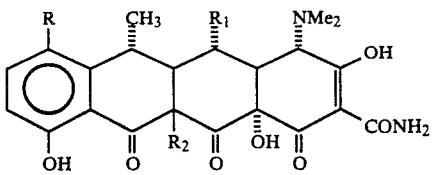

wherein

R and $R_2$ are each hydrogen or chloro, and $R_1$ is hydrogen or hydroxyl.

The preceding compouns are produced by hydrogenation of the corresponding 6-methylenetetracycline compounds of the formula:

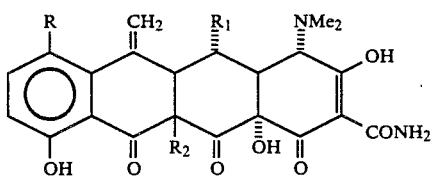

wherein R, $R_1$ and $R_2$ are as defined above.

The 6-methylenetetracyclines which are thus reacted may be prepared in the manner known in the art, e.g., as described in Blackwood U.S. Pat. No. 2,984,986 granted May 6, 1961.

The transition metal complexes utilized in the process of the present invention are also known materials described, for example, in the above-noted prior art (e.g., J. Org. Chem. 36, 752–757 (1971); U.S. Pat. No. 3,703,561; Chim. Ind. Milan, 58 (10), 732 (1976); and British Patent 2,025,403). It is preferred to utilize as such transition metal complex $CuCl(PPh_3)_2$; the latter material may be prepared by reacting a copper salt, preferably cuprous chloride, with a phosphine, preferably triphenyl phosphine, according to the method of G.W.J. Fleet et al described in Tetrahedron Lett. 11,975-8(1979).

The hydrogenation reaction is carried out in the manner known in the art, with the stereospecific formation of the desired alpha epimer in yields in excess of 95%. HPLC analyses of the hydrogenation products indicate the absence of beta-epimer and methacycline contents of less than 0.3%. The hydrogenation is effected in the presence of about 5 to about 30 millimoles of the transition metal complex in admixture with a trace amount of rhodium, suitably from about 0.25 to about 2.5 millimoles of rhodium (preferably as rhodium chloride or rhodium-on-carbon), per mole of the 6-methylenetetracycline reacted. Preferably, the transition metal complex is admixed with the trace rhodium in the proportion of from about 12 to about 20 moles of the complex pe: mole of rhodium (as the metal). The amount of rhodium admixed with the transition metal complex thus varies from about 1/10 to 1/350th of that required in previously described alpha-6-deoxytetracycline syntheses. Accordingly, the catalytic hydrogenation of the present invention provides superior yields and purities of the desired alpha-6-deoxytetracyclines, with substantially improved efficiencies of operation.

The reaction is suitably carried out in a lower alkanol solvent, preferably methanol, ethanol, propan-1-ol, propan-2-ol or butanol. The solvents are degassed with nitrogen prior to use.

The reaction time depends on the amount of catalyst and the type of autoclave used for the hydrogenation. Normally, to obtain high yields and purities, reaction times of from about 3 to 16 hours are utilized. It is preferred, but not critical, to carry out the reaction under pressures ranging from about 4 to 12 kg/cm$^2$, and at temperatures of from about 50° to 90° C. At temperatures lower than about 50° C. the reaction is too slow, and at higher temperatures decomposition occurs.

The doxycycline or other alpha-epimer is crystallized as an acid addition salt from the reaction mixture, preferably in the form of the sulfosalicylate or p-toluene sulfonate salt (by adding excess sulfosalicycic acid or p-toluene sulfonic acid). The purity is more than 99.5% by HPLC. The doxycycline sulfosalicylate or p-toluene sulfonate is thereafter converted directly to doxycycline hyclate (the hemiethanolate hemihydrate) in stoichiometric yield by procedures known in the art.

Alternatively, the reductive dehalogenation and hydrogenation can be carried out by a two-step technique, initially effecting lla-reductive dehalogenation with a conventional catalyst, e.g. 5% Rh/C or 5% Pd/C in methanol. The initial catalyst is then removed by filtration, and the solution is again subjected to hydrogenation in the presence of the catalyst system of the present invention.

In the following examples, particularly preferred embodiments of the hydrogenation catalyst and the process for the preparation of alpha-6-deoxytetracyclines therewith are described. In the examples, all temperatures are given in degrees Celsius and all parts and percentages by weight, unless otherwise specified.

EXAMPLE 1

Preparation of Chloro Bis (Triphenylphosphine) Copper (I)

To a vigorously stirred suspension of triphenylphosphine (108 g, 0.412 mole) in chloroform (700 ml) was added copper(I) chloride (20 g, 0.203 mole) portionwise over a period of 10 minutes. The reaction mixture was stirred at 35°–40° for another 15 minutes. The organic layer was washed thoroughly with water (2×100 ml). Ethanol (1000 ml) was added to the chloroform layer. Immediately, a white solid precipitated out which was filtered, washed with ethanol and dried at 110° C. for 3 hours. Yield 110 g (87%) m.pt. 176–78° C. Found C, 69.9; H, 4.9; Cl, 5.5; Cu, 9.7; P, 9.5; Calc. C, 69.3; H, 4.8; Cu, 10.1; P 9.9; Cl, 5.7%)

EXAMPLE 2

Production Of Doxycycline From Methacycline Hydrochloride With Chloro Bis (Triphenylphosphine) Copper (I) and Hydrated Rhodium Trichloride Methacycline hydrochloride (100 g, 0.21 mole), Cu-(I)Cl(PPh$_3$)$_2$ (0 76 g, 1.22 mM) prepared as described in Example 1, rhodium trichloride (15 mg, 0.057 mM) and methanol (600 ml) were charged to a stainless steel hydrogenation vessel. The reactants were hydrogenated at 80°–85° and at a pressure of 85–90 psi for 8 hrs. p-Toluene sulfonic acid (89.8 g, 0.52 mole) was added to the reaction mixture, and the mixture was stirred for 5 hours at room temperature. Doxycycline p-toluene sulfonate (PTS) separated out immediately and was then filtered, washed with chilled methanol (100 ml) and dried at 55°-60° C. The product weighed 127.0 g (98.6%).

The doxycycline PTS was dissolved in ethanol (500 ml) and conc. hydrochloric acid (65 ml) and treated with activated charcoal (3.0 g) for 2 minutes. The reaction mixture was filtered through a G-4 sintered funnel. The filtrate was agitated at 55°-60° C. for 90 minutes. It was cooled to 20°-25° C., filtered, washed with acetone (100 ml), and dried. The resulting doxycycline hyclate weighed 90.2 g (85.3%). HPLC analysis indicated: alpha epimer 99.69%, beta epimer none, methacycline 0.17% and other materials 0.14%. A second crop was obtained as doxycycline sulfosalicylate (SSA) (18.0 g) by the addition of sulfosalicyclic acid to the mother liquor.

The yield, stereospecificity and purity of the product obtained in Example 2 is compared with those claimed in corresponding examples of various prior art doxycycline synthesis patents in the following table:

Comparison of the Production of Doxycycline as Described in Example 2 With Prior Art Processes

| Pat. No. | Example | Rhodium used Per kg of MOT.HCl | Yield[d] (%) | Alpha Isomer | Beta Isomer | MOT | Purity of isolated product (%) |
|---|---|---|---|---|---|---|---|
| U.S. 4,207,258 | 2 | 19540 | 78.0 | NS | NS | NS | 99.3[b] |
| French 2,216,268 | 3 | 21252 | 90.6 | NS | NS | NS | NS |
| U.S. 3,954,862 | 3 | 1962 | 80.0 | 81.0* | 1.6* | NS | NS[a] |
| U.S. 4,001,321 | 1 | 9369 | 95.0 | 93.0 | 2.0–3.0* | NS | 93.0[b] |
| U.S. 3,962,131 | 2 | Less than 3332.4 | 98.8 | NS | NS | NS | 99.7[b] |
| U.S. 3,907,890 | 5 | 0 | 75.2 | 98.0 | 2.0 | 0 | 98.0[a] |
| Re. 32,535 | 4 | 620.6 | 99.1 | 99.89 | 0 | 0 | 99.89[c] |
| Present invention | 2 | 60.0 | 98.6 | 99.69 | Nil | 0.14 | 99.69[a] |

*Values in the reaction mixture
NS: Not stated
MOT: 6-deoxy-6-demethyl-6-methylene-5-oxytetracycline (methacycline)
[a]HPLC analysis
[b]UV analysis
[c]Paper chromatography
[d]Examples with highest yields considered for comparison purposes.

From the table it will be seen that the only prior art processes which resulted in the formation of doxycycline products in yields, stereospecificities, and purities which even approached those obtained in Example 2 (the processes of U.S. Pat. No. 3,962,131 and Re. 32,535), required from ten to as much as fifty times the amount of rhodium utilized in Example 2. Use of the procedure of the present invention thus provides substantially and unexpectedly superior economies relative to each of the noted prior art procedures.

EXAMPLE 3

Example 2, when repeated with Cu(I)Cl(PPh$_3$)$_2$ (2.0 g, 3.2 mM), prepared as described in Example 1, and rhodium chloride (15 mg, 0.057 mM), yielded doxycycline PTS (125 g, 97.1%). The quality of the product was comparable to that obtained in Example 2.

EXAMPLE 4

Example 2 was repeated with Cu(I)Cl(PPh$_3$)$_2$ (4.0 g, 6.4 mM), prepared as described in Example 1, and 1.0 g 5% Rh/C. Doxycycline p-toluene sulfonate was isolated (117.0 g, 90.8%) and converted into doxycycline hyclate (82.0 g, 84%) as described in Example 2. HPLC of the product showed alpha epimer 99.5%, beta epimer none, methacycline 0.2% and other materials 0.28%.

EXAMPLE 5

Production of Doxycycline by Conversion of 11a-Chloro Methacycline PTS Salt to Methacycline With Rh/C, Followed by Conversion of the Methacycline to Doxycycline With Chloro (Bis) (Triphenylphosphine) Copper (I) and 5% Rh/C)

11a-chloro methacycline PTS salt (100 g, 0.154 m) and 5% Rh/C (1.25 g) in methanol (600 ml) were charged to the stainless steel hydrogenation vessel. The contents were hydrogenated at 35°-40° C. under a pressure of 2.0 kg/cm$^2$ until absorption of hydrogen ceased (3 hours). Thin layer chromatography and HPLC of the reaction mixture showed almost pure methacycline. The Rh/C catalyst was filtered off and the filtrate was subjected to hydrogenation in the presence of Cu-(I)Cl(PPh$_3$)$_2$ )$_2$ (4.0 g, 6.4 mM) and 5% Rh/C (1.0 g, 0.48 mM). Hydrogenation was carried out under the same temperature and pressure conditions employed in Example 2. Doxycycline PTS (71.5 g, 75.5%) was isolated. The product quality was comparable with that obtained in Example 2.

EXAMPLE 6

11a-chloro methacycline PTS salt (40 g, 0.062 mole) hydrogenation vessel. The contents were hydrogenated at 35°-40° C. under a pressure of 2.0 kg/cm$^2$ until hydrogen absorption ceased (3 hours). Thin layer chromatography and HPLC of the reaction mixture showed almost pure methacycline. The Rh/C catalyst was filtered off and the filtrate was subjected to hydrogenation in the presence of Cu(I)Cl(PPh$_3$)$_2$ (1.6 g, 2.5 mM), prepared as described in Example 1, and hydrated rhodium trichloride (5.0 mg, 0.019 mM). Hydrogenation was carried out under the conditions of temperature and pressure employed in Example 2. Doxycycline PTS (31.5 g, 83.18%) was obtained.

CONTROL A

Hydrogenation of Methacycline Hydrochloride With Chloro (Bis) Triphenylphosphine Copper (I) Alone Methacycline hydrochloride (50.0 g, 0.105 mole), and Cu(I)Cl(PPh$_3$)$_2$ (2 g, 3.2 mM) prepared as described in Example 1, were hydrogenated under the conditions of Example 2. Thin layer chromatography of the reaction mixture showed the presence of methacycline only. Doxycycline was not detected.

CONTROL B

Hydrogenation of Methacycline With Rhodium Chloride Alone

Methacycline hydrochloride (50.0 g, 0.105 mole) and rhodium chloride (8.0 mg, 0.03 mM) were hydrogenated under the conditions of Example 2. Thin layer chromatography of the reaction mixture showed the presence of methacycline only. Doxycycline was not detected.

EXAMPLE 7

Preparation of Co(II)Cl$_2$(PPh$_3$)$_2$

Triphenylphosphine (10.49 g, 0.04 mole) in boiling butanol (100 ml) was added to a solution of cobalt chloride hexahydrate (4.76 g, 0.02 mole) in boiling butanol (100 ml). On cooling, the pure product separated as a crystalline solid which was filtered off, washed with butanol and dried in a vacuum desiccator. Yield 82% (Found: C, 66.3; H, 4.6; Calc. C, 66.0; H, 4.58%) m.pt. 234°–36° C.(dec.)

EXAMPLE 8

Production of Doxycycline From Methacycline Hydrochloride With Chloro Bis (Triphenylphosphine) Cobalt (II) and Rhodium Trichloride Methacycline hydrochloride (50 g, 0.105 mole), Co(III)Cl$_2$(PPh$_3$)$_2$ (0.4 g, 0.61 mM), and rhodium chloride (8 mg, 0.03 mM) were hydrogenated under the temperature and pressure conditions employed in Example 2. Doxycycline p-toluene sulfonate (61.5 g, 95.5%) was isolated. The product quality was comparable to the product obtained in Example 2.

EXAMPLE 9

Preparation of Ni(II)Cl$_2$(PPh$_3$)$_2$

Triphenylphosphine (10.49 g, 0.04 mole) in boiling butanol (100 ml) was added to a solution of nickel chloride hexahydrate (4.76 g, 0.02 mole) in boiling butanol (100 ml). On cooling, the pure product separated as dark blue crystals which were filtered off, washed with butanol and dried in a vacuum desiccator. Yield 84% (Found: C, 66.0; H, 4.7; Calc. for C$_{36}$H$_{30}$Cl$_2$NiP$_2$: C, 66.1; H, 4.6%). M.pt. 246°–50° C. (dec.)

EXAMPLE 10

Production of Doxycycline From Methacycline Hydrochloride With Chloro Bis (Triphenylphosphine) Nickel II and Rhodium Trichloride Example 8 was repeated using Ni(II)Cl$_2$(PPh$_3$)$_2$ prepared as described in Example 9. Doxycycline p-toluene sulfonate (61.8 g, 96%) was isolated. The product quality was comparable to that obtained in Example 2.

It will be understood that various changes may be made in the preferred catalyst embodiments and process parameters described hereinabove without departing from the scope of the present invention. Accordingly, it is intended that the invention is not limited to the preceding description but should be construed in the light of the following claims:

We claim:

1. In a process for the preparation of an alpha-6-deoxytetracycline by the hydrogenation of a substrate selected from the group consisting of a 6-deoxy-6-demethyl-6-methylenetetracycline and a salt thereof, the improvement comprising conducting the hydrogenation in the presence of a hydrogenation catalyst comprising a transition metal complex of the formula MCl$_x$(PPh$_3$)$_y$, wherein M is copper, nickel or cobalt, x=1–2 and y=1–3, in the transition metal complex being formed in the presence of chloroform and apart from the hydrogenation of the substrate the presence of a catalytic amount of rhodium.

2. The process of claim 1, wherein rhodium is present as rhodium chloride.

3. The process of claim 1, wherein rhodium is present as rhodium metal-on-carbon.

4. The process of claim 1, wherein the hydrogenation is carried out in the presence of from 0.25 to 2.5 millimoles of rhodium in said catalyst per mole of said substrate.

5. The process of claim 1, wherein the hydrogenation is carried out in the presence of from 5 to 30 millimoles of the transition metal complex, per mole of substrate.

6. The process of claim 1, wherein the hydrogenation is carried out under pressures of from 4 to 12 kg/cm$^2$ and at temperatures of from 50° to 90° C., and the alpha-6-deoxytetracycline is recovered in the form of the sulfosalicyclate or p-toluene sulfonate salt thereof.

7. The process of claim 1 for producing doxycycline, wherein the substrate is methacycline, or an acid addition salt thereof.

8. The process of claim 7, wherein the substrate is methacycline or 11a-chloro methacycline.

9. The process of claim 1, wherein the transition metal complex is chloro bis (triphenylphosphine) copper (I).

10. The process of claim 1, wherein the transition metal complex is chloro bis (triphenylphosphine) cobalt (II).

11. The process of claim 1, wherein the transition metal complex is chloro bis (triphenylphosphine) nickel (II).

* * * * *

UNITED STATES PATENT AND TRADEMARK OFFICE
CERTIFICATE OF CORRECTION

PATENT NO. : 4,997,959

DATED : March 5, 1991

INVENTOR(S) : J. KHANNA et al

It is certified that error appears in the above-identified patent and that said Letters Patent is hereby corrected as shown below:

Column 2, line 5:   delete "solely" and substitute --only--

Column 3, line 19:  delete "Compouns" and substitute --Compounds--

Column 4, line 62:  delete (0 76g, 1.22mM) and insert --(0.76g, 1.22mM)--

Column 6, line 47:  after (40g. 0.062 mole) insert --and 5% Rh/C(0.5g) in Methanol (240 ml) were charged to the--

Column 8, line 26:  delete "in" (first occurrence)

Column 8, line 29:  after "substrate", insert --in--

Signed and Sealed this

Twenty-sixth Day of January, 1993

Attest:

STEPHEN G. KUNIN

*Attesting Officer*   Acting Commissioner of Patents and Trademarks